United States Patent [19]

Robertson

[11] Patent Number: 4,973,597

[45] Date of Patent: Nov. 27, 1990

[54] ANTICONVULSANT AGENTS

[75] Inventor: David W. Robertson, Greenwood, Ind.

[73] Assignee: Eli Lilly and Company, Indianapolis, Ind.

[21] Appl. No.: 374,680

[22] Filed: Jun. 30, 1989

[51] Int. Cl.$^5$ ............... A61K 31/455; C07D 213/46
[52] U.S. Cl. ................... 514/354; 514/355; 546/316; 546/323
[58] Field of Search ............... 546/316, 323; 514/355, 514/354

[56] References Cited

U.S. PATENT DOCUMENTS

| | | | |
|---|---|---|---|
| 2,799,679 | 7/1957 | Ekenstam et al. | 546/316 |
| 3,462,532 | 8/1969 | Hardy | 546/316 |
| 4,001,416 | 1/1977 | Pommei et al. | 514/355 |
| 4,004,029 | 1/1977 | Collins et al. | 514/619 |
| 4,031,105 | 6/1977 | Chimeno | 546/316 |
| 4,361,572 | 11/1982 | Takaku et al. | 546/262 |
| 4,638,014 | 1/1987 | Clark | 514/619 |
| 4,684,748 | 8/1987 | Robertson | 514/619 |
| 4,743,610 | 5/1988 | Wright et al. | 514/357 |

FOREIGN PATENT DOCUMENTS

| | | |
|---|---|---|
| 279633 | 8/1988 | European Pat. Off. . |
| 2611601 | 9/1977 | Fed. Rep. of Germany . |
| 2726200 | 1/1978 | Fed. Rep. of Germany . |

OTHER PUBLICATIONS

Moffett et al., J. Med. Chem., 14(10), 963 (1971).
Clark et al., J. Med. Chem., 29, 1534 (1986).
Robertson et al., J. Med. Chem., 20, 1742 (1987).

*Primary Examiner*—Jane T. Fan
*Attorney, Agent, or Firm*—Robert A. Conrad; Leroy Whitaker

[57] ABSTRACT

This invention provides certain pyridinecarboxamide derivatives, their pharmaceutical formulations, and their use as anticonvulsant agents.

12 Claims, No Drawings

ANTICONVULSANT AGENTS

BACKGROUND THE INVENTION

The several anticonvulsant drugs marketed in the United States provide significant seizure relief for only 50–75% of epileptic patients. The therapeutic effects are sometimes accompanied by serious side effects such as sedation, ataxia, psychoses, suicidal depression, gastrointestinal disturbances, gingival hyperplasia, lymphadenopathies, megaloblastic anemias, hepatotoxicity, nephropathies, hirsutism, and fetal malformations. These side effects, which range in severity from mild sedation to death from aplastic anemia, are particularly troublesome since most of the marketed anticonvulsants have very low therapeutic ratios. For example, phenytoin, one of the most widely used anticonvulsants, controls seizures in man only when plasma levels reach 10 mcg/ml. Toxic effects such as nystagmus are seen at around 20 mcg/ml, ataxia is obvious at 30 mcg/ml, and lethargy is apparent at about 40 mcg/ml. See "The Pharmacological Basis of Therapeutics" (Gilman, Goodman, and Gilman, ed., 6th Ed., MacMillan Publishing Co., Inc., New York, New York (1980)), p. 455. In view of these facts, most epileptologists indicate there is a definite need for more selective and less toxic anticonvulsant drugs.

SUMMARY OF THE INVENTION

This invention provides pyridinecarboxamides of the Formula I

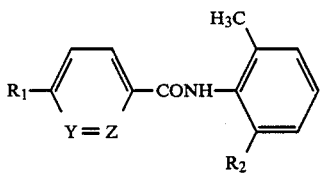

and pharmaceutically-acceptable salts thereof wherein $R_1$ is methyl, ethyl, chloro, methoxy, methylthio, or methylamino;

$R_2$ is methyl or chloro; and one of Y and Z is N and the other of Y and Z is CH.

This invention also provides a method for treating and preventing convulsions in mammals in need of such treatment which comprises administering to said mammal an effective amount of a pyridinecarboxamide of Formula I.

According to a further aspect of the present invention, there are provided pharmaceutical formulations which comprise as active ingredient a pyridinecarboxamide of Formula I in association with a pharmaceutically acceptable carrier or diluent.

DETAILED DESCRIPTION AND PREFERRED EMBODIMENT

The present invention relates to organic compounds that are useful for treating and preventing convulsions in mammals.

The preferred compounds of this invention are those wherein Y is N, Z is CH, and $R_2$ is methyl. The most preferred compounds are those wherein $R_1$ is methylamino or especially methyl.

The pharmaceutically acceptable acid addition salts of this invention can be prepared by standard methods known in the art employing those acids of sufficient acidity to form acid addition salts of the nicotinamide compounds of Formula I. These include salts derived from inorganic acids such as hydrochloric acid, nitric acid, phosphoric acid, sulfuric acid, hydrobromic acid, hydriodic acid, phosphorous acid and the like, as well as salts derived from organic acids such as aliphatic mono- and di-carboxylic acids, phenyl-substituted alkanoic acids, hydroxy-alkanoic and -alkanedioic acids, aromatic acids, aliphatic and aromatic sulfonic acids, etc. Such pharmaceutically acceptable salts thus include sulfate, metaphosphate, pyrophosphate, chloride, bromide, iodide, fluoride, oxalate, maleate, benzenesulfonate, toluenesulfonate, chlorobenzenesulfonate, methanesulfonate, propanesulfonate, naphthalene-1-sulfonate, naphthalene-2-sulfonate and the like. The Preferred salts are those derived from inorganic acids, especially hydrochloric acid.

Certain of the compounds of Formula I can be prepared by standard acylation procedures well known in the art as summarized by the following scheme:

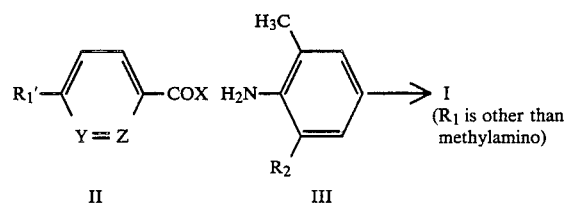

wherein X is bromo, chloro, or —OH and $R_1'$ is methyl, ethyl, chloro, methoxy, or methylthio.

Any of a number of general acylation techniques may be employed. One method is the reaction of an acid halide (II, X is bromo or chloro) and the aniline (III) in a nonreactive solvent, such as tetrahydrofuran or dimethylformamide, preferably in the presence of an acid scavenger such as a carbonate, especially potassium carbonate, or an organic base, such as triethylamine or pyridine. Although it is preferred that the reactants be added in the approximate molar ratio of about 1.25:1 (II:III), other ratios are operative. The reaction is carried out from about room temperature up to the reflux temperature of the reaction mixture. Under the preferred conditions of approximately 25° C., the reaction is generally complete in 1–2 hours.

Standard coupling techniques employing carboxylic acids (III, X=—OH) may also be employed using coupling reagents such as DCC, EEDQ, CDI, etc.

The preferred method of preparing compounds of Formula I according to the scheme above involves the reaction of a pyridinecarboxylic acid (II,X=OH) with an alkyl haloformate, such as ethyl chloroformate, in the presence of a non-reactive acid scavenger, perferably an organic base such as triethylamine, and a non-reactive solvent, such as acetone. This conversion to the mixed anhydride is best carried out at temperatures from about −20° C. to about 20° C. The resulting mixed anhydride solution is then treated with aniline III. Transformation to the desired product I is usually complete within 12–18 hours when the mixture is kept at a temperature from about 20°–30° C.

The methylamino substituted compounds of this invention may be prepared from the corresponding chloro compound (ie, a compound of Formula I where $R_1$ is chloro) by reacting with methylamine. In general, this reaction is accomplished by reacting a large excess of the amine with the chloro compound, preferably in the presence of a non-reactive solvent such as ethanol or the like. The reaction is generally carried out at temperatures from about 50°-250° C. in a sealed reaction vessel. At the reaction temperature of 250° C., the reaction is generally complete within approximately 72 hours.

The intermediates of Formulas II and III and other necessary reagents for preparing the compounds employed in this invention are commercially available, are known in the art, or can be prepared by methods taught in the literature.

The pyridinecarboxamides of Formula I are anticonvulsant agents and may be administered by various routes including the oral, rectal, transdermal, subcutaneous, intravenous, intramuscular, or intranasal routes, being usually employed in the form of a pharmaceutical composition. It is a special feature of these compounds that they are effective following oral administration. The invention includes a pharmaceutical composition comprising from about 1% to about 95% by weight of a compound of Formula I, or a pharmaceutically acceptable acid addition salt thereof, associated with a pharmaceutically acceptable carrier.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The compositions are preferably formulated in a unit dosage form, each dosage containing from about 5 to 500 mg, more usually 25 to 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with the required pharmaceutical carrier.

The active compounds are effective over a wide dosage range. For example, dosages per day will normally fall within the range of about 0.5 to 300 mg/kg of body weight. In the treatment of adult humans, the range of about 1 to 50 mg/kg, in single or divided doses, is preferred. However, it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms.

The following examples further illustrate the preparation of the compounds and formulations employed in this invention. The examples are illustrative only and are not intended to limit the scope of the invention in any way.

EXAMPLE 1

6-Chloro-N-(2,6-dimethylphenyl)-3-pyridinecarboxamide

A slurry of 25 g of 6-chloronicotinic acid in approximately 300 ml of acetone was treated with 22.6 ml of triethylamine. The reaction mixture was cooled to approximately −10° C. by means of an external ice/methanol bath. A solution of 15.5 ml of ethyl chloroformate in acetone was added to the mixture at a rate to maintain the temperature below 0° C. After stirring with the cold bath for 2 hours, a solution of 38.5 g of 2,6-dimethylaniline in approximately 150 ml of acetone was added while maintaining the temperature below 0° C. After the addition was complete, the mixture was allowed to warm to room temperature overnight. The mixture was poured into water and extracted into ethyl acetate. The organic layer was washed with water, dilute hydrochloric acid, water, a dilute sodium bicarbonate solution, water (twice), and a saturated sodium chloride solution. The organic solution was dried over sodium sulfate and concentrated in vacuo to provide 30.5 g of a solid. Crystallization from methanol/water provided 14.6 g of the desired title product, m.p. 165°-166° C.

Analysis for $C_{14}H_{13}ClN_2O$: Calculated: C, 64.50; H, 5.03; N, 10.74; Found: C, 64.34; H, 5.27; N, 10.55.

EXAMPLES 2-3

The following compounds were prepared from the appropriate nicotinic acid derivative and corresponding analine according to the procedure of Example 1.

2. N-(2,6-Dimethylphenyl)-6-methyl-3-pyridinecarboxamide, 30% yield, m.p. 164°-165° C.

Analysis for $C_{15}H_{16}N_2O$: Calculated: C, 74.97; H, 6.71; N, 11.66; Found: C, 74.75; H, 6.43; N, 11.44.

3. N-(2-Chloro-6-methylphenyl)-6-methyl-3-pyridinecarboxamide, 7% yield, m.p. 111°-112° C.

Analysis for $C_{14}H_{13}ClN_2O$: Calculated: C, 64.50; H, 5.03; N, 10.74; Found: C, 64.74; H, 5.30; N, 10.80.

EXAMPLE 4

6-(Methylamino)-N-(2,6-dimethylphenyl)-3-pyridinecarboxamide

A solution of 5 g of 6-chloro-N-(2,6-dimethylphenyl)-3-pyridinecarboxamide and 6 g of methylamine (from a 40% aqueous solution) in 100 ml of ethanol were heated at 250° C. in a closed reaction vessel for 72 hours. The reaction mixture was cooled to room temperature, solvents were removed under reduced pressure, and the product was recrystallized from ethanol, providing 2.8 g of the desired title product, m.p. 207°-209° C.

Analysis for $C_{15}H_{17}N_3O$: Calculated: C, 70.56; H, 6.71; N, 16.46; Found: C, 70.43; H, 6.85; N, 16.36.

The following formulation examples may employ as active compounds any of the pharmaceutical compounds of Formula I or their pharmaceutically acceptable salts.

EXAMPLE 5

Hard gelatin capsules are prepared using the following ingredients:

|  | Quantity (mg/capsule) |
|---|---|
| 5-Chloro-N-(2,6-dimethylphenyl)-2-pyridinecarboxamide | 250 |
| Starch dried | 200 |
| Magnesium stearate | 10 |

The above ingredients are mixed and filled into hard gelatin capsules in 460 mg quantities.

EXAMPLE 6

A tablet formula is prepared using the ingredients below:

|  | Quantity (mg/tablet) |
|---|---|
| N-(2,6-Dimethylphenyl)-5-methoxy-2-pyridinecarboxamide | 250 |
| Cellulose, microcrystalline | 400 |
| Silicon dioxide, fumed | 10 |
| Stearic acid | 5 |

The components are blended and compressed to form tablets each weighing 665 mg.

EXAMPLE 7

An aerosol solution is prepared containing the following components:

|  | Weight % |
|---|---|
| N-(2,6-dimethylphenyl)-5-methyl-amino-2-pyridinecarboxamide | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

EXAMPLE 8

Tablets each containing 60 mg of active ingredient are made up as follows:

| N-(2-Chloro-6-methylphenyl)-5-methyl-amino-2-pyridinecarboxamide | 60 mg |
|---|---|
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°-60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLE 9

Capsules each containing 80 mg of medicament are made as follows:

| N-(2-Chloro-6-methylphenyl)-6-methyl-amino-3-pyridinecarboxamide | 80 mg |
|---|---|
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

EXAMPLE 10

Suppositories each containing 225 mg of active ingredient are made as follows:

| N-(2-Chloro-6-methylphenyl)-5-methyl-thio-2-pyridinecarboxamide | 225 mg |
|---|---|
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 11

Suspensions each containing 50 mg of medicament per 5 ml dose are made as follows:

| N-(2,6-Dimethylphenyl)-6-methylthio-3-pyridinecarboxamide | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

The compounds of Formula I are anticonvulsant agents with a large therapeutic ratio and long half-life and are therefore useful in the treatment and prevention of convulsions in mammals. Moreover, the compounds have a lessened propensity to interact with drug metabolizing enzymes compared to certain anticonvulsant amides. The compounds are effective against tonic extensor seizures elicited by maximal electroshock and should therefore be useful for treating generalized tonic-clonic ("grand mal"), cortical focal, complex partial (temporal lobe epilepsy), simple partial (focal motor), and post-traumatic seizures in humans. This activity is demonstrated in the electroshock induced convulsion inhibition assay which follows.

In the electroshock induced convulsion inhibition assay (E.S.), the compound to be tested was suspended in acacia and administered by gavage to each of ten Cox standard strain albino male mice (18-24 g) at the dose level being investigated. Thirty to 180 minutes after compound administration, the mice were subjected to a 0.2 second, 50 milliampere electroshock through corneal electrodes. The animals were examined and evaluated immediately after the electroshock for the occurrence of clonic, flexor tonic, or extensor tonic convulsions, or death and the $ED_{50}$ was determined for each compound as the dose which inhibited the occurrence of extensor tonic convulsions in one half of the animals immediately after the electroshock. For comparison, 18 milliamperes was usually sufficient to produce extensor tonic convulsions in about half of the control animals; at 50 milliamperes, almost all control animals (receiving vehicle only) died. The test results summarized in Table I are reported as the $ED_{50}$ values calculated by computer interpolation of fixed doses at the time interval found to provide an optimal response after dosing. For comparison purposes, N-(2,6-dimethylphenyl)-3-pyridinecarboxamide, taught as an intermediate in Example 4 of U.S. Pat. No. 4,361,572, was also evaluated—this compound is referred to in Table I below as Compound A.

TABLE I

| Anti-convulsant Activity of compounds of Formula I | | |
|---|---|---|
| Example No. | Electroshock $ED_{50}$ (mg/kg)* | Time after dosing (minutes)** |
| 1 | 31.7 | 30 |
| 2 | 6.7 | 60 |
| 3 | 20.2 | 60 |
| 4 | 8.7 | 60 |
| Compound A | 24.49 | 30 |

*oral dose (gavage)—See text for methodology.
**Time (between dosing and administration of the electroshock) providing an approximately optimal response.

I claim:

1. A compound of the Formula

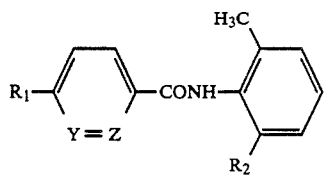

or a pharmaceutically-acceptable salt thereof wherein
$R_1$ is methyl, ehtyl, methoxy, methylthio, or methylamino;
$R_2$ is methyl or chloro; and
one of Y and Z is N and the other of Y and Z is CH.

2. A compound of claim 1 wherein $R_2$ is methyl.

3. A compound of claim 2 wherein Y is N and Z is CH.

4. The compound of claim 3 which is N-(2,6-dimethylphenyl)-6-methyl-3-pyridinecarboxamide or a pharmaceutically acceptable acid addition salt thereof.

5. A method for treating or preventing convulsions in mammals in need of such treatment which comprises administering to said mammal an effective amount of a compound of claim 1.

6. The method of claim 5 employing a compound wherein $R_2$ is methyl.

7. The method of claim 6 employing a compound wherein Y is N and Z is CH.

8. The method of claim 7 employing the compound N-(2,6-dimethylphenyl)-6-methyl-3-pyridinecarboxamide or a pharmaceutically acceptable acid addition salt thereof.

9. A pharmaceutical formulation useful for the treatment of convulsions which comprises a compound of claim 1 and one or more pharmaceutically-acceptable excipients, carriers, or diluents therefor.

10. A formulation according to claim 9 employing a compound wherein $R_2$ is methyl.

11. A formulation according to claim 10 employing a compound wherein Y is N and Z is CH.

12. A formulation according to claim 11 employing N-(2,6-dimethylphenyl)-6-methyl-3-pyridinecarboxamide or a pharmaceutically acceptable acid addition salt thereof.

* * * * *